| United States Patent [19] | [11] Patent Number: 4,847,381 |
| Sutherland et al. | [45] Date of Patent: Jul. 11, 1989 |

[54] 2-PHENYL-4-QUINOLINE CARBOXYLIC ACIDS

[75] Inventors: Leslie H. Sutherland, Dallas, Tex.; Adolph E. Sloboda; Ralph G. Child, both of Rockland, N.Y.; John F. Poletto, Bergen, N.J.; Dennis W. Powell, Rockland, N.Y.

[73] Assignee: American Cyanamid Company, Stamford, Conn.

[21] Appl. No.: 90,996

[22] Filed: Aug. 31, 1987

[51] Int. Cl.[4] .................... A61K 31/47; C07D 215/20
[52] U.S. Cl. .................................... 546/156; 548/485
[58] Field of Search .............. 546/152, 153, 156, 170, 546/173; 514/311, 312

[56] References Cited

U.S. PATENT DOCUMENTS

| 2,008,923 | 7/1935 | Ornstein | 546/173 |
| 2,077,903 | 4/1937 | Schlichenmaier | 546/153 |
| 2,524,741 | 10/1950 | Tulagin | 546/170 |
| 2,579,420 | 12/1951 | Coles | 546/170 |
| 2,886,436 | 5/1959 | Schmidt | 546/156 |
| 2,888,346 | 5/1959 | Tulagin | 546/173 |
| 3,574,840 | 4/1971 | Riviere | 514/311 |
| 4,009,020 | 2/1977 | Starke | 71/94 |
| 4,680,299 | 7/1987 | Hesson | 514/311 |

FOREIGN PATENT DOCUMENTS

| 2304270 | 8/1973 | Fed. Rep. of Germany | 546/173 |
| 1109402 | 8/1984 | U.S.S.R. | 546/153 |

OTHER PUBLICATIONS

John et al. (1932) J. Prakt. Chem., vol. 133, pp. 259–272.
Kost et al. (1971) Khim. Geterotsikl. Soedin., 7 (9), pp. 1214–1217.
Munson et al. (1975) J. Med. Chem., 18 (12), pp. 1232–1236.

*Primary Examiner*—Anton H. Sutto
*Assistant Examiner*—Mark W. Noel
*Attorney, Agent, or Firm*—Edward A. Conroy; Alan M. Gordon

[57] ABSTRACT

Substituted 4-quinoline-carboxylic acids useful in the treatment of arthritis and inhibition of progressive joint deterioration are disclosed together with methods of use and synthesis thereof.

9 Claims, No Drawings

2-PHENYL-4-QUINOLINE CARBOXYLIC ACIDS

BRIEF SUMMARY OF THE INVENTION

This invention is concerned with methods of (a) treating arthritis in a mammal by inhibiting the progressive joint deterioration characteristic of arthritic disease, and (b) inducing immunosuppression in a mammal which comprise administering to said mammal an effective amount of a compound of the formula:

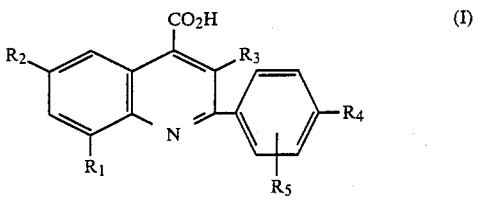

wherein $R_1$ is hydrogen, halogen or alkyl($C_1$–$C_3$); $R_2$ is hydrogen, halogen, trifluoromethyl or alkyl($C_1$–$C_3$); $R_3$ is hydroxy or alkanlyloxy($C_2$–$C_6$); $R_4$ is halogen, hydroxy, alkyl($C_1$–$C_6$), trifluoromethyl, cycloalkyl($C_3$–$C_6$), phenyl, benzyl, phenoxy, phenylthio, 2,4-dichlorophenoxy or mono-and di-substituted phenyl wherein the substituents are halogen or alkoxy($C_1$–$C_3$); and $R_5$ is hydrogen or halogen; in association with a pharmacologically acceptable carrier.

In addition, this invention is also concerned with novel compounds of the formula (I) wherein $R_1$, $R_2$, $R_3$, $R_4$ and $R_5$ are as therein defined but with the proviso that when $R_1$ is hydrogen, $R_2$ is other than fluoro, and $R_3$ is hydroxy then $R_4$ may not be chloro, bromo, iodo, methyl or phenyl.

DETAILED DESCRIPTION OF THE INVENTION

The compounds of formula (I) may be readily prepared in accordance with the following reaction scheme:

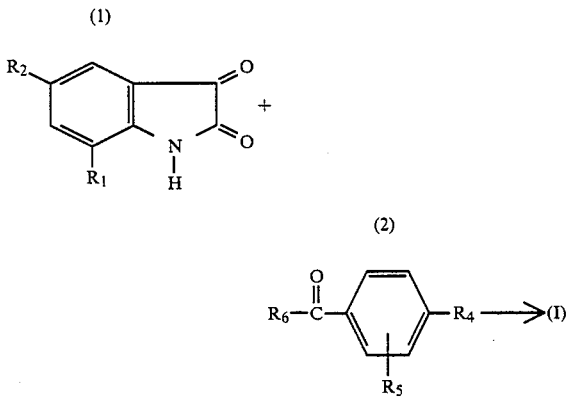

wherein $R_1$, $R_2$, $R_4$ and $R_5$ are as hereinbefore defined and $R_6$ is —$C_2H_5$ or —$CH_2OCO$-alkyl($C_1$–$C_5$). With reference to the above reaction scheme, an appropriately substituted 2,3-indolinedione (1) in aqueous solution made basic with an alkali metal hydroxide and warmed, is mixed with a lower alkanolic solution of an appropriately substituted acetophenone (2), and the resulting reaction mixture is held at the reflux temperature for several hours. During this process, a portion of the lower alkanol is removed by distillation, the residue is heated further at reflux, then cooled and filtered and the filtrate acidified where-upon the desired product (I) precipitates. The product (I) is then collected by filtration and, if necessary, recrystallized by conventional procedures.

The compounds of the present invention are active immunosuppressive agents when administered to warm-blooded animals. As such they are effective in treating conditions where elevated levels of antibody production or monocyte/lymphocyte activity as a result of the hyperreactivity of the immunoregulatory network are closely associated with the development of autoimmune diseases, including rheumatoid arthritis [Mellbye, O.J. and Natvig, J.B., Clin. Exp. Immunol., 8, 889 (1971)], multiple sclerosis [Tourtellotte, W.W. and Parker, J.A., Science 154, 1044 (1966)], systemic lupus erythematosis [Abdu, N. I., et al., Clin. Immunol. Immunopath., 6, 192 (1976)], thyroiditis [Witebsky, E., et al., J. Immunol., 103, 708 (1969)], mixed connective tissue disease [Sharp, G. C., et al., Am. J. Med., 52, 148 (1972)], dermato-/polymyositis [Venables, P.J.W., et al., Ann. Rheum. Dis., 40, 217 (1981)], insulin-dependent diabetes [Charles, M. A., et al., J. Immunol., 130, 1189 (1983)] and in patients undergoing organ transplantation.

The immunosuppressive activity of the compounds of this invention was established in the following test.

ACUTE GRAFT-VS.-HOST REACTION

An acute graft-vs.-host (GvH) reaction was induced in normal B6D2F1 male mice by the intravenous injection of $30$–$50 \times 10^6$ parental spleen cells of the C57BL/6 parent. Ten days post GvH induction the B6D2F1 mice were acutely immunosuppressed. On day 10, spleen cells from the B6D2F1 mice were removed aseptically, placed in tissue culture and stimulated with T-cell mitogen [Concanavalin-A (Con-A)]at a concentraion of 2 $\mu$g/ml. The ability of the spleen cells to proliferate in response to the mitogen was determined by pulse labeling of dividing cells with $^3$H-thymidine for the last 24 hours of the 72 hour tissue culture period. The labeled cells were harvested on millipore filters and the amount of $^3$H radioactivity was quantitated with a liquid scintillation spectrometer. Drug dosing began on the day of GvH induction and continued through the 10 day in vivo protocol. The test compounds were administered orally in a phosphate buffer pH 7.4 vehicle containing 0.025M phosphate, 0.075M sodium chloride and 0.002% polysorbate 20. The data from drug dosed mice was compared with GvH mice dosed with vehicle and with normal mice. A compound is considered active if it reduced the degree of suppression seen in the Con-A proliferative response of vehicle treated GvH mice compared with normal mice.

The results of this test on representative compounds of this invention appear in Table I.

TABLE I

| Compound | Graft-vs.-Host Reaction | | | |
|---|---|---|---|---|
| | Dose (mg/kg) | GvH | Con-A Response $^3$H cpm | Percent Suppression |
| None | — | — | 120386 | — |
| Vehicle | — | + | 32428 | 73 |
| 2-(4-Chlorophenyl)-3-hydroxy-6-iodo-4-quinolinecarboxylic acid | 50 | + | 96487 | 20 |
| None | — | — | 295315 | — |
| Vehicle | — | + | 169220 | 43 |
| 2-[1,1'-Biphenyl]-4-yl- | 50 | + | 278001 | 6 |

TABLE I-continued

Graft-vs.-Host Reaction

| Compound | Dose (mg/kg) | GvH | Con-A Response $^3$H cpm | Percent Suppression |
|---|---|---|---|---|
| 6-bromo-3-hydroxy-4-quinolinecarboxylic acid | | | | |
| None | — | — | 181886 | — |
| Vehicle | — | + | 17161 | 91 |
| 3-(Acetyloxy)-2-[1,1'-biphenyl]-4-yl-4-quinolinecarboxylic acid | 50 | + | 128187 | 29 |
| None | — | — | 295315 | — |
| Vehicle | — | + | 169220 | 43 |
| 3-Hydroxy-6-methyl-2-[1,1'-biphenyl]-4-yl-4-quinolinecarboxylic acid | 50 | + | 285448 | 3 |
| None | — | — | 157509 | — |
| Vehicle | — | + | 74145 | 53 |
| 6-Fluoro-3-hydroxy-2-[1,1'-biphenyl]-4-yl-4-quinolinecarboxylic acid | 50 | + | 139289 | 12 |
| None | — | — | 248699 | — |
| Vehicle | — | + | 28206 | 89 |
| 2-(4-Chlorophenyl)-6-fluoro-3-hydroxy-4-quinolinecarboxylic acid | 25 | + | 183441 | 26 |
| None | — | — | 157509 | — |
| Vehicle | — | + | 74145 | 53 |
| 6-Fluoro-2-(2'-fluoro-[1,1'-biphenyl]-4-yl)-3-hydroxy-4-quinolinecarboxylic acid | 50 | + | 129464 | 18 |

In addition these compounds are effective in treating inflammation and joint destruction associated with arthritic disease in warm-blooded animals as established in the following test.

INDUCTION OF ADJUVANT ARTHRITIS

Outbred, male, Royalhart Wistar rats (Royalhart Farms, New Hampton, N.Y.), weighing approximately 165 g, were injected intradermally in the right hind paw with killed and dried Mycobacterium tuberculosis emulsified in mineral oil (adjuvant) at a dose of 2 mg/kg of body weight. This protocol for induction of arthritis has been described in detail by A.E. Sloboda and A.C. Osterberg, Inflammation, 1, 415 (1976).

Seven days subsequent to immunization with the adjuvant, the rats were divided into groups and treated daily by gavage with various doses of the test compounds. Control groups of rats were immunized with adjuvant, but then treated only with starch vehicle.

At the end of 23 days post adjuvant immunization, the left hin paw diameters of all the rats were measured around the ankle joint with a vernier caliper.

The results of this test on representative compounds of this invention are shown in Table II.

The statistical significance of differences between control and treated group were calculated using Students test.

TABLE II

Treatment of Adjuvant Induced Arthritis

| Compound | Daily Dose mg/kg | Number of Animals | Final Rat Wt. (gm) | Arthritic Paw Diameter (mm) |
|---|---|---|---|---|
| Arthritic Controls pooled) | — | 446 | 244 | 11.8 |
| 2-(4-Chlorophenyl)-3-hydroxy-6-iodo-4-quinolinecarboxylic acid | 50 | 15 | 276 | 9.0* |
| 6-Chloro-2-(4-chlorophenyl)-3-hydroxy-4-quinolinecarboxylic acid | 50 | 8 | 275 | 7.5* |
| 2-[1,1'-Biphenyl]-4-yl-3-hydroxy-4-quinolinecarboxylic acid | 12.5 | 15 | 303 | 7.8* |
| 2-(4-Chlorophenyl)-3-hydroxy-4-quinolinecarboxylic acid | 50 | 17 | 291 | 9.0* |
| 2-[1,1'-Biphenyl]-4-yl-6-bromo-3-hydroxy-4-quinolinecarboxylic acid | 12.5 | 17 | 267 | 8.6* |
| 2-(4-Bromophenyl)-3-hydroxy-6-iodo-4-quinolinecarboxylic acid | 25 | 11 | 244 | 9.9* |
| 3-Hydroxy-2-(4-iodophenyl)-4-quinolinecarboxylic acid | 50 | 15 | 314 | 9.3* |
| 3-(Acetyloxy)-2-[1,1'-biphenyl]-4-yl-4-quinolinecarboxylic acid | 12.5 | 14 | 319 | 7.7* |
| 3-Hydroxy-6-methyl-2-[1,1'-biphenyl]-4-yl-4-quinolinecarboxylic acid | 12.5 | 17 | 317 | 8.4* |
| 6,8-Dichloro-3-hydroxy-2-[1,1'-biphenyl]-4-yl-4-quinolinecarboxylic acid | 12.5 | 13 | 301 | 8.4* |
| 3-Hydroxy-8-methyl-2-[1,1'-biphenyl]-4-yl-4-quinolinecarboxylic acid | 50 | 12 | 291 | 7.6* |
| 6-Fluoro-3-hydroxy-2-[1,1'-biphenyl]-4-yl-4-quinolinecarboxylic acid | 3.13 | 8 | 284 | 9.68* |
| 2-(3,4-Dichlorophenyl)-3-hydroxy-6-methyl-4-quinolinecarboxylic acid | 50 | 14 | 269 | 9.2* |
| 2-(4-Chlorophenyl)-6-fluoro-3-hydroxy-4-quinolinecarboxylic acid | 25 | 13 | 276 | 8.1* |
| 3-(Acetyloxy)-2-[1,1'-biphenyl]-4-yl-6-bromo-4-quinolinecarboxylic acid | 6.25 | 17 | 325 | 9.0* |
| 6-Fluoro-2-(2'-fluoro-[1,1'-biphenyl]-4-yl)-3-hydroxy-4-quinolinecarboxylic acid | 6.25 | 17 | 273 | 8.1* |
| 6-Bromo-2-(4-chlorophenyl)-3-hydroxy-4-quinolinecarboxylic acid | 50 | 14 | 295 | 8.1* |
| 6,8-Dichloro-2-(4-chlorophenyl)-3-hydroxy-4-quinolinecarboxylic acid | 50 | 12 | 271 | 8.4* |
| 2-(4-Chlorophenyl)-3-hydroxy-6-methyl-4-quinolinecarboxylic acid | 50 | 14 | 275 | 9.0* |
| 6-Bromo-3-hydroxy-2-(4-iodophenyl)-4-quinolinecarboxylic acid | 50 | 14 | 322 | 8.7* |
| 6-Fluoro-2-(4-fluorophenyl)-3-hydroxy-4-quinolinecarboxylic acid | 25 | 17 | 273 | 10.5* |
| 6-Bromo-3-hydroxy-2-(4'-methoxy[1,1'-biphenyl]-4-yl)-4-quinolinecarboxylic acid | 50 | 17 | 290 | 8.3* |
| 6-Bromo-2-(4-fluorophenyl)-3-hydroxy-4-quinolinecarboxylic acid | 50 | 12 | 271 | 9.0* |
| 2-(2,4-Difluorophenyl)- | 50 | 14 | 300 | 8.2* |

TABLE II-continued

Treatment of Adjuvant Induced Arthritis

| Compound | Daily Dose mg/kg | Number of Animals | Final Rat Wt. (gm) | Arthritic Paw Diameter (mm) |
|---|---|---|---|---|
| 6-fluoro-3-hydroxy-4-quinolinecarboxylic acid | | | | |
| 6-Bromo-2-(2,4-difluorophenyl)-3-hydroxy-4-quinolinecarboxylic acid | 50 | 15 | 270 | 8.9* |
| 6-Chloro-3-hydroxy-2-(4'-methoxy[1,1'-biphenyl]-4-yl)-4-quinolinecarboxylic acid | 50 | 15 | 269 | 7.3* |
| 6-Fluoro-3-hydroxy-2-(4'-methoxy[1,1'-biphenyl]-4-yl)-4-quinolinecarboxylic acid | 25 | 17 | 286 | 8.4* |
| 6,8-Dichloro-2-(3,4-dichlorophenyl)-3-hydroxy-4-quinolinecarboxylic acid | 25 | 7 | 298 | 8.1* |
| 6,8-Dichloro-3-hydroxy-2-(4-iodophenyl)-4-quinolinecarboxylic acid | 50 | 12 | 276 | 8.6* |

*Statistically significant suppression of arthritic paw diameter relative to the arthritic controls. p = <.05 by students t test.

p The inhibition of progressive joint deterioration was demonstrated by the following test.

INHIBITION OF PROGRESSIVE JOINT DESTRUCTION

This protocol is identical to the experiment whose results were described in Table I. At the end of 23 days the rats were killed, their left hind paws amputated and radiographic evaluation was made as follows: Joint roentgraphs of the left hind paws were prepared on Polaroid x-ray film (type 55) using a Faxitron x-ray unit (Model 43805-N, Hewlett Packard, McMinnville, OR). The focus to film distance was 45cm and the exposure to the x-ray source was 5 minutes at 60KVP. Each radiograph was graded (blind) for the presence and severity of the following parameters:
(a) juxtaarticular erosions of the tarsal bones; and
(b) cartilage space narrowing.

A grade of 0 to 4 (with=normal and 4'severe changes) was assigned to each of the parameters.

Again the statistical significance between arthritic controls and treated rats were determined by the use of Students t test. The results of this test on representative compounds of this invention are shown in Table III.

TABLE III

Inhibition of Induced Joint Deterioration

| Compound | Daily Dose mg/kg | No. of Animals | X-Ray Scores Erosions | X-Ray Scores Cartilage Space |
|---|---|---|---|---|
| Arthritic Controls (historical) | — | 9,668 | 3.12 | 3.27 |
| 2-(4-Chlorophenyl)-3-hydroxy-6-iodo-4-quinolinecarboxylic acid | 50 | 15 | 1.86* | 2.29* |
| 6-Chloro-2-(4-chlorophenyl)-3-hydroxy-4-quinolinecarboxylic acid | 50 | 8 | 1.17* | 1.67* |
| 2-[1,1'-Biphenyl]-4-yl-3-hydroxy-4-quinolinecarboxylic acid | 12.5 | 15 | 2.07* | 1.67* |
| 2-(4-Chlorophenyl)-3-hydroxy-4-quinolinecarboxylic acid | 50 | 17 | 1.53* | 1.94* |
| 2-[1,1'-Biphenyl]-4-yl-6-bromo-3-hydroxy-4-quinolinecarboxylic acid | 12.5 | 17 | 1.64* | 2.16* |
| 3-Hydroxy-2-(4-iodophenyl)-4-quinolinecarboxylic acid | 50 | 15 | 1.57* | 2.00* |
| 3-(Acetyloxy)-2-[1,1'-biphenyl]-4-yl-4-quinolinecarboxylic acid | 12.5 | 14 | 1.64* | 1.64* |
| 3-Hydroxy-6-methyl-2-[1,1'-biphenyl]-4-yl-4-quinolinecarboxylic acid | 12.5 | 17 | 2.03* | 1.97* |
| 6,8-Dichloro-3-hydroxy-2-[1,1'-biphenyl]-4-yl-4-quinolinecarboxylic acid | 12.5 | 13 | 2.46* | 2.38* |
| 3-Hydroxy-8-methyl-2-[1,1'-biphenyl]-4-yl-4-quinolinecarboxylic acid | 50 | 12 | 1.95* | 2.32* |
| 6-Fluoro-3-hydroxy-2-[1,1'-biphenyl]-4-yl-4-quinolinecarboxylic acid | 3.13 | 16 | 1.94* | 2.13* |
| 2-(3,4-Dichlorophenyl)-3-hydroxy-6-methyl-4-quinolinecarboxylic acid | 50 | 14 | 2.29* | 2.21* |
| 2-(4-Chlorophenyl)-6-fluoro-3-hydroxy-4-quinolinecarboxylic acid | 25 | 13 | 1.21* | 1.42* |
| 3-(Acetyloxy)-2-[1,1'-biphenyl]-4-yl-6-bromo-4-quinolinecarboxylic acid | 6.25 | 17 | 1.71* | 2.06* |
| 6-Fluoro-2-(2'-fluoro-[1,1'-biphenyl]-4-yl)-3-hydroxy-4-quinolinecarboxylic acid | 6.25 | 17 | 2.53* | 1.53* |
| 6-Bromo-2-(4-chlorophenyl)-3-hydroxy-4-quinolinecarboxylic acid | 50 | 14 | 2.19* | 1.69* |
| 6,8-Dichloro-2-(4-chlorophenyl)-3-hydroxy-4-quinolinecarboxylic acid | 50 | 12 | 2.17* | 1.75* |
| 2-(4-Chlorophenyl)-3-hydroxy-6-methyl-4-quinolinecarboxylic acid | 50 | 14 | 2.07* | 1.43* |
| 6-Bromo-3-hydroxy-2-(4-iodophenyl)-4-quinolinecarboxylic acid | 50 | 14 | 2.07* | 1.86* |
| 6-Fluoro-2-(4-fluorophenyl)-3-hydroxy-4-quinolinecarboxylic acid | 25 | 17 | 2.6* | 2.8 |
| 6-Bromo-3-hydroxy-2-(4'-methoxy[1,1'-biphenyl]-4-yl)-4-quinolinecarboxylic acid | 50 | 17 | 1.65* | 1.59* |
| 6-Bromo-2-(4-fluorophenyl)-3-hydroxy-4-quinolinecarboxylic acid | 50 | 12 | 2.17* | 2.42* |
| 2-(2,4-Difluorophenyl)-6-fluoro-3-hydroxy-4-quinolinecarboxylic acid | 50 | 14 | 2.5* | 1.79* |
| 6-Bromo-2-(2,4-difluorophenyl)-3-hydroxy-4-quinolinecarboxylic acid | 50 | 15 | 1.0* | 1.67* |
| 6-Chloro-3-hydroxy-2-(4'-methoxy[1,1'-biphenyl]-4-yl)-4-quinolinecarboxylic acid | 50 | 15 | 1.67* | 0.60* |
| 6-Fluoro-3-hydroxy-2-(4'-methoxy[1,1'-biphenyl]-4-yl)-4-quino- | 25 | 17 | 2.22* | 0.89* |

TABLE III-continued

Inhibition of Induced Joint Deterioration

| Compound | Daily Dose mg/kg | No. of Animals | X-Ray Scores | |
|---|---|---|---|---|
| | | | Erosions | Cartilage Space |
| linecarboxylic acid | | | | |

*Statistically significant suppression of arthritic paw diameter relative to the arthritic controls. p = <.05 by students t test.

The compounds of this invention may be orally administered to treat arthritis, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of the active compound. The percentage of active compound in these compositions may, of course, be varied and may conveniently be between about 2% to about 60% of the weight of the unit. The amount of active compound in such therapeutically useful compositions is such that a suitable dosage will be obtained. Preferred compositions according to this invention are prepared so that an oral dosage unit contains between about 50 and 250 mg of active compound.

The tablets, capsules and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetning agent such as sucrose, lactose or saccharin.

When the dosage unit form is a capsule it may contain, in addition to materials of the above type, a liquid carrier such as a fatty oil.

Various other materials may be present as coatings or to otherwise modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and flavoring such as cherry or orange flavor.

These active compounds may also be administered parenterally. Solutions or suspensions of these active compounds can be prepared in water suitably mixed with a surfactant such as hydroxypropylcelllose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The invention will be described in greater detail in conjuncton with the following specific examples,

EXAMPLE 1

2-(4-Chlorophenyl)-3-hydroxy-6-iodo-4-quinolinecarboxylic acid

This compound was prepared by the method of Marshall and Blanchard, J. Pharmacol., 95, 185 (1949), mp 199.5°–200° C.

The compounds of Examples 2–12, named below, were made by the same procedure.

| Example | Name | MP° C. |
|---|---|---|
| 2 | 6-Chloro-2-(4-chlorophenyl)-3-hydroxy-4-quinolinecarboxylic acid | 212–214 |
| 3 | 2-[1,1'-Biphenyl]-4-yl-3-hydroxy-4-quinolinecarboxylic acid | 196–201 |
| 4 | 2-(4-Chlorophenyl)-3-hydroxy-4-quinolinecarboxylic acid | 211–212 |
| 5 | 2-[1,1'-Biphenyl]-4-yl-6-bromo-3-hydroxy-4-quinolinecarboxylic acid | 225 |
| 6 | 3-Hydroxy-6-methyl-2-(4-methylphenyl)-4-quinolinecarboxylic acid | 155–157 |
| 7 | 2-(4-Bromophenyl)-3-hydroxy-6-iodo-4-quinolinecarboxylic acid | 214.5–215.5 |
| 8 | 2-(4-Bromophenyl)-3-hydroxy-4-quinolinecarboxylic acid | 248–249 |
| 9 | 3-Hydroxy-6-iodo-2-(4-iodophenyl)-4-quinolinecarboxylic acid | 228–230 |
| 10 | 6-Bromo-2-(4-bromophenyl)-3-hydroxy-4-quinolinecarboxylic acid | 216–217 |
| 11 | 6,8-Dibromo-2-(4-bromophenyl)-3-hydroxy-4-quinolinecarboxylic acid | 212–213 |
| 12 | 3-Hydroxy-2-(4-iodophenyl)-4-quinolinecarboxylic acid | 253–255 |

EXAMPLE 13

3-(Acetyloxy)-2-[1-1'-biphenyl]-4-yl-4-quinolinecarboxylic acid

A 10.4 g portion of 2-[1,1'-biphenyl]-4-yl-3-hydroxy-4-quinolinecarboxylic acid was treated with 50 ml of acetic anhydride and 20 drops of concentrated sulfuric acid. The mixture was heated for ½ hour on a steam bath with occasional swirling, then poured into 300 ml of ice water, stirred and treated with sodium bicarbonate solution until weakly acid. The solid was collected, washed with water, dried and recrystallized from 400 ml of ethanol, giving 6.0 g of the desired product as yellow-orange crystals, mp 199°14 200° C.

EXAMPLE 14

2-[1,1'-biphenyl]-4-yl-6-fluoro-3-[(1-oxohexyl)oxy]-4-quinolinecarboxylic acid

A suspension of 3.59 g. of 6-fluoro-3-hydroxyl-2-(1,1'-biphenyl)-4--quinolinecarboxylic acid in 17 mL of hexanoic anhydride was treated with 6 drops of sulfuric acid. The mixture was stirred (over-head) and heated at 100° C. (steam-bath) for 3 hours. The reaction mixture was cooled and poured over 100 g. of ice. The aqueous suspension was neutralized to pH=7 with 5N NaOH. After stirring for 15 min., the ester was extracted from the aqueous phase with ethyl acetate (200 mL). The organic extract was washed with brine, dried over magnesium sulfate, filtered and then concentrated to approximately 25 mL. The resulting crystalline solid was collected, washed with cold ethylacetate and air-dried to afford 2.2 g of the desired product, m.p. 179°–206° C.

EXAMPLE 15

2-[1,1'-biphenyl]-4-yl-6-fluoro-3-[(1-oxopentyl)oxy]-4-quinolinecarboxylic acid

A suspension of 3.59 g. of 6-fluoro-3-hydroxy-2-(1,1'-biphenyl)-4--quinolineacarboxylic acid in 17 mL of valeric anhydride was treated with 6 drops of sulfuric acid. The mixture was stirred (over-head) and heated at 100° C. (steam-bath) for 3 hours. The reaction mixture was cooled and poured over 100 g of ice. The aqueous suspension was neutralized to pH=7 with 5N NaOH. After stirring for 15 min., the ester was extracted from the aqueous phase with ethyl acetate (200 mL). The organic extract was washed with brine, dried over magnesium sulfate, filtered and then concentrated to approximately 25 mL. The resulting crystalline solid was collected, washed with cold ethylacetate and air-dried to afford 3.0 g. of the desired product, m.p. 214°–217° C.

EXAMPLE 16

2-[1,1'-biphenyl[-4-yl-3-(2,2-dimethyl-1-oxopropoxy-)-6-fluoro--4-quinolineacarboxylic acid A suspension of 3.59 g. of 6-fluoro-3-hydroxy-2-(1,1-biphenyl)-4--quinolinecarboxylic acid in 17 mL of trimethylacetic anhydride was treated with 6 drops of sulfuric acid. The mixture was stirred (over-head) and heated at 100° C. (steam-bath) for 3 hours. The reaction mixture was cooled and poured over 100 g. of ice. The aqueous suspension was neutralized to pH=7 with 5N NaOH. After stirring for 15 min., the ester was extracted from the aqueous phase with ethylacetate (200 mL). The organic extract was washed with brine, dried over magnesium sulfate, filtered and then concentrated to approximately 15 mL. The resulting crystallilne solid was collected washed with cold ethylacetate and air-dried to afford 2.8 g of the desired product, m.p. 215°–217° C.

EXAMPLE 17

2-[1,1'-biphenyl]-4-yl-3-(2-methyl-1-oxopropoxy)-6-fluoro-4-quinolinecarboxylic acid A suspension of 2.5 g. of 6-fluoro3-hydroxy-2-(1,1'-biphenyl)-4--quinolinecarboxylic acid in 20 mL of isobutyric anhydride was treated with 6 drops of sulfuric acid. The mixture was stirred (over-head) and heated at 100° C. (steam-bath) for 3 hours. The reaction mixture was cooled and poured over 100 g. of ice. The aqueous suspension was neutralized to pH=7 with 5N NaOH. After stirring for 15 min., the ester was extracted from the aqueous phase with ethylacelate (200 mL). The organic extract was washed with brine, dried over magnesium sulfate, filtered and then concentrated to approximately 15 mL. The resulting crystalline solid was collected, washed with cold ethylacetate and air-dried to afford 0.7 g of the desired product, m.p. 201°–204° C.

EXAMPLE 18

2-[1,1'-biphenyl]-4-yl-3-(1-oxobutoxy)-4-quinolinecarboxylic acid

A suspension of 3.0 g of 3-hydroxy-2-(1,1'-biphenyl)-4-quinolinecarboxylic acid in 15 mL of butyric anhydride was treated with 6 drops of sulfuric acid. The mixture was stirred (over-head) and heated at 100° C. (steam-bath) for 3 hours. The reaction mixture was cooled and resulting crystalline solid was collected, washed with cold ethylacetate and air-dried to afford 2.0 g of the de sired product, m.p. 195°–196° C.

EXAMPLE 19

3-Hydroxy-6-methyl-2-[1,1'-biphenyl]-4-yl-4-quinolinecarboxylic acid

A mixture of 30 g of 5-methyl-2,3-indolinedione in 200 ml of water and 30.6 g of sodium hydroxide in 100 ml of water was reacted with a solution of 47.4 g of acetoxyacetylbiphenyl in 500 ml of ethanol. The mixture was refluxed for 3 hours, then 250 ml of ethanol was removed by distillation. A 500 ml portion of water was added, The mixture was stirred, cooled to room temperature and filtered through diatomaceous earth. The filtrate was acidified with 60 ml of concentrated hydrochloric acid and 20 ml of glacial acetic acid. The resulting solid was collected, taken up in dilute ammonia and the insoluble portion collected. This solid was dissolved in 7.4N ammonia, filtered and precipitated with glacial acetic acid, giving 32.0 g of the desired product, mp 236°–238° C.

EXAMPLE 20

6,8-Dichloro-3-hydroxy-2-[1,1'-biphenyl]-4-yl-4-quinolinecarboxylic acid

A suspension of 21 g of 5,7-dichloro-2,3-indolinedione in 120 ml of water was treated with a sufficient amount of a solution of 16.6 g of sodium hydroxide in 55 ml of water to provide solution. A warm solution of 25.4 g of acetoxyacetylbiphenyl in 350 ml of ethanol was added, followed by the balance of the alkali solution. The mixture was refluxed for 2.5 hours. During the last ½ hour 50 ml of ethanol was distilled off. A 300 ml portion of water was added, the mixture was stirred, cooled and filtered through diatomaceous earth. The solid was taken up in 1500 ml of water containing 100 ml of 10N sodium hydroxide, filtered and the filtrate treated with 32 ml of concentrated hydrochloric acid and 10 ml of glacial acetic acid. The resulting solid was dissolved in 400 ml of hot cellosolve, filtered and precipitated with water, giving 18.5 g of the desired product, mp 215°–217° C.

EXAMPLE 21

3-Hydroxy-8-methyl-2-[1,1'-biphenyl]-4-yl-4-quinolinecarboxylic acid

A suspension of 16.1 g of 7-methyl-2,3-indolinedione in 120 ml of water was treated with a sufficient amount of a solution of 16.6 of sodium hydroxide in 55 ml of water to provide solution. A warm solution of 25.4 g of acetoxyacetylbiphenyl in 350 ml of ethanol was added, followed by the balance of the alkali solution. The mixture was refluxed for 2.5 hours. During the last ½ hour 50 ml of ethanol was distilled off. A 300 ml portion of water was added, the mixture was stirred, cooled and filtered through diatomaceous earth. The filtrate was treated with 34 ml of concentrated hydrochloric acid and 12 ml of glacial acetic acid. The resulting solid was collected and recrystallized from ethanol/water, giving 13.6 g of the desired product, mp 178°–180° C.

EXAMPLE 22

6-Fluoro-3-hydroxy-2-[1,1'-biphenyl]-4-yl-4-quinolinecarboxylic acid

A suspension of 6.6 g of 5-fluoro-2,3-indolinedione in 48 ml of water was treated with a sufficient amount of a solution of 6.62 g of sodium hydroxide in 22 ml of water to provide solution. A warm solution of 10.17 g of acetoxyacetylbiphenyl in 80 ml of ethanol was added, followed by the balance of the alkali solution. The mixture was refluxed for 3 hours. During the last ½ hour 10 ml of ethanol was distilled off. A 103 ml portion of water was added, the mixture was stirred, cooled and filtered through diatomaceous earth. The filtrate was treated with 13.6 ml of concentrated hydrochloric acid and 4.39 ml of glacial acetic acid and stirred for 30 minutes. The resulting precipitate was collected, washed with water and ether and air dried. The resulting solid was stirred and heated in 400 ml of ethanol. The solid was collected, washed with water and dried giving 11.2 g of the desired product, mp 25220 –254° C.

EXAMPLE 23

2-(3,4-Dichlorophenyl)-3-hydroxy-6-methyl-4-quinolinecarboxylic acid

A suspension of 16.1 g of 5-methyl-2,3-indolinedione in 120 ml of water was treated with a sufficient amount of a solution of 16 g of sodium hydroxide in 60 ml of water to provide solution. A warm solution of 24.7 g of 3,4-dichloro-2-hydroxyacetophenone, acetate in 250 ml of ethanol was added followed by the balance of the alkali solution. The mixture was refluxed for 3 hours and 75 ml of alcohol was distilled off. The mixture was cooled, treated wth 300 ml of water, stirred and filtered through diatomaceous earth. The filtrate was acidified with 33 ml of concentrated hydrochloric acid and 12 ml of glacial acetic acid, cooled for 3 hours and the resulting solid collected. This solid was dissolved in 800 ml of boiling methyl cellosolve, treated with charcoal, filtered and cooled. This solid was collected, giving 10.2 g of the desired product, mp 250° C. (dec.).

Following the general procedures described in Examples 13–23, the compounds listed in the following Table IV as Examples 24–56 were prepared.

TABLE IV

| Ex. | 2,3-Indolinedione | Acetyl Derivative | Product | MP °C. |
|---|---|---|---|---|
| 24 | 6-Fluoro- | 4-Chloro-2-hydroxyacetophenone, acetate | 2-(4-Chlorophenyl)-6-fluoro-3-hydroxy-4-quinolinecarboxylic acid | 210–212 |
| 25 | 6-Bromo- | Acetoxyacetylbiphenyl | 3-(Acetyloxy)-2-[1,1'-biphenyl]-4-yl-6-bromo-4-quinolinecarboxylic acid | 271–275 |
| 26 | 6-Fluoro- | 4-(2'-Fluorophenyl)-phenacylacetate | 6-Fluoro-2-(2'-fluoro[1,1'-biphenyl]-4-yl)-3-hydroxy-4-quinolinecarboxylic acid | 212–214 |
| 27 | 6-Bromo- | 4-Chloro-2-hydroxyacetophenone, acetate | 6-Bromo-2-(4-chlorophenyl)-3-hydroxy-4-quinolinecarboxylic acid | 201–203 |
| 28 | 6,8-Dichloro- | 4-Chloro-2-hydroxyacetophenone, acetate | 6,8-Dichloro-2-(4-chlorophenyl)-3-hydroxy-4-quinolinecarboxylic acid | 214–216 |
| 29 | 6-methyl- | 4-Chloro-2-hydroxyacetophenone, acetate | 2-(4-Chlorophenyl)-3-hydroxy-6-methyl-4-quinolinecarboxylic acid | 247–248 |
| 30 | 6-Bromo- | 4-Iodo-2-hydroxyacetophenone, acetate | 6-Bromo-3-hydroxy-2-(4-iodophenyl)-4-quinolinecarboxylic acid | 242–244 |
| 31 | 6-Fluoro- | 4-Fluoro-2-hydroxyacetophenone, acetate | 6-Fluoro-2-(4-fluorophenyl)-3-hydroxy-4-quinolinecarboxylic acid | 220–224 |
| 32 | 6-Bromo- | 4-(4'Methoxyphenyl)-propiophenone | 6-Bromo-3-hydroxy-2-(4'-methoxy-[1,1'-biphenyl]-4-yl)-4-quinolinecarboxylic acid | 245–247 |
| 33 | 6-Bromo- | 4-Fluoro-2-hydroxyacetophenone, acetate | 6-Bromo-2-(4-fluorophenyl)-3-hydroxy-4-quinolinecarboxylic acid | 195–197 |
| 34 | 6-Fluoro- | 2,4-Difluoro-2-hydroxyacetophenone, acetate | 2-(2,4-Difluorophenyl)-6-fluoro-3-hydroxy-4-quinolinecarboxylic acid | 207–208 |
| 35 | 6-Bromo- | 2,4-Difluoro-2-hydroxyacetophenone, acetate | 6-Bromo-2-(2,4-difluorophenyl)-3-hydroxy-4-quinolinecarboxylic acid | 208–209 |
| 36 | 6-Chloro- | 4-(4'-Methoxyphenyl)-propiophenone | 6-Chloro-3-hydroxy-2-(4'-methoxy-[1,1'-biphenyl]-4-yl)-4-quinolinecarboxylic acid | 215–218 |
| 37 | 6-Fluoro- | 4-(4'-Methoxyphenyl)-propiophenone | 6-Fluoro-3-hydroxy-2-(4'-methoxy-[1,1'-biphenyl]-4-yl)-4-quinolinecarboxylic acid | 253–255 |
| 38 | 6,8-Dichloro- | 3,4-Dichloro-2-hydroxyacetophenone, acetate | 6,8-Dichloro-2-(3,4-dichlorophenyl)-3-hydroxy-4-quinolinecarboxylic acid | 264–266 |
| 39 | 6,8-Dichloro- | 4-Iodo-2-hydroxyacetophenone, acetate | 6,8-Dichloro-3-hydroxy-2-(4-iodophenyl)-4-quinolinecarboxylic acid | 270–272 |
| 40 | 6-Fluoro- | 2-(Acetyloxy)-1-(4-phenoxyphenyl)ethanone | 6-Fluoro-3-hydroxy-2-(4-phenoxyphenyl)-4-quinolinecarboxylic acid | 201–203 |
| 41 | Unsubstituted | 2-(Acetyloxy)-1-(4-phenoxyphenyl)ethanone | 3-Hydroxy-2-(4-phenoxyphenyl)-4-quinolinecarboxylic acid | 200–201 |
| 42 | 6-Methyl- | 2-(Acetyloxy)-1-(4-phenoxyphenyl)ethanone | 3-Hydroxy-6-methyl-2-(4-phenoxyphenyl)-4-quinolinecarboxylic acid | 197–198 |
| 43 | 6-Bromo- | 2-(Acetyloxy)-1-(4-phenoxyphenyl)ethanone | 6-Bromo-3-hydroxy-2-(4-phenoxyphenyl)-4-quinolinecarboxylic acid | 264–267 |
| 44 | 6-Fluoro- | 2-(Acetyloxy)-1-[4-(phenylmethyl)phenyl]-ethanone | 6-Fluoro-3-hydroxy-2-[4-(phenylmethyl)phenyl]-4-quinolinecarboxylic acid | 194–196 |
| 45 | 6-Fluoro- | 2-(Acetyloxy)-1-[4-(phenylthio)phenyl]- | 6-Fluoro-3-hydroxy-2-[4-(phenylthio)phenyl]-4-quinolinecarboxylic acid | 196–198 |

TABLE IV-continued

| Ex. | 2,3-Indolinedione | Acetyl Derivative | Product | MP °C. |
|---|---|---|---|---|
| 46 | 6-Bromo- | 2-(Acetyloxy)-1-[4-(phenylthio)phenyl]-ethanone | 6-Bromo-3-hydroxy-2-(4-phenylthio)phenyl]-4-quinolinecarboxylic acid | 182–184 |
| 47 | 6-Fluoro- | 2-(Acetyloxy-1-[4-(1,1-dimethylethyl)phenyl]-ethanone | 2-[4-(1,1-Dimethylethyl)phenyl]-6-fluoro-3-hydroxy-4-quinolinecarboxylic acid | 206–207 |
| 48 | Unsubstituted | 2-(Acetyloxy)-1-[ 4-(phenylmethyl)phenyl]-ethanone | 3-Hydroxy-2-[4-(phenylmethyl)phenyl]-4-quinolinecarboxylic acid | 187–189 |
| 49 | Unsubstituted | 2-(Acetyloxy)-1-[4-(2,4-dichlorophenoxy)phenyl]-ethanone | 2-[4-(2,4-Dichlorophenoxy)phenyl]-3-hydroxy-4-quinolinecarboxylic acid | 201–203 |
| 50 | 6-Fluoro- | 2-(Acetyloxy)-1-[4-(2,4-dichlorophenoxy)phenyl]-ethanone | 2-[4-(2,4-Dichlorophenoxy)phenyl]-6-fluoro-3-hydroxy-4-quinolinecarboxylic acid | 196–199 |
| 51 | 6-Bromo- | 2-(Acetyloxy)-1-[4-(phenylmethyl)phenyl]-ethanone | 6-Bromo-3-hydroxy-2-[4-(phenylmethyl)phenyl]-4-quinolinecarboxylic acid | 192–194 |
| 52 | 6-Bromo- | 2-(Acetyloxy)-1-[4-(2,4-dichlorophenoxy)phenyl]-ethanone | 6-Bromo-2-[4-(2,4-dichlorophenoxy)phenyl]-3-hydroxy-4-quinolinecarboxylic acid | 190–192 |
| 53 | Unsubstituted | 2-(Acetyloxy)-1-(4-cyclohexylphenyl)-ethanone | 2-(4-Cyclohexylphenyl)-3-hydroxy-4-quinolinecarboxylic acid | 264–268 |
| 54 | 6-Methyl- | 2-(Acetyloxy)-1-(4-cyclohexylphenyl)-ethanone | 2-(4-Cyclohexylphenyl)-3-hydroxy-6-methyl-4-quinolinecarboxylic acid | 285–288 |
| 55 | 6-Bromo- | 2-(Acetyloxy)-1-(4-cyclohexylphenyl)-ethanone | 6-Bromo-2-(4-cyclohexylphenyl)-3-hydroxy-4-quinolinecarboxylic acid | 288–291 |
| 56 | 6-Fluoro- | 2-(Acetyloxy)-1-(4-cyclohexylphenyl)ethanone | 2-(4-Cyclohexylphenyl)-3-hydroxy-6-fluoro-4-quinolinecarboxylic acid | 265–267 |

What is claimed is:

1. A compound of the formula:

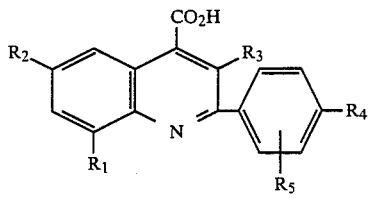

wherein $R_1$ is hydrogen, halogen or alkyl($C_1$–$C_3$); $R_2$ is hydrogen, halogen, trifluoromethyl or alkyl($C_1$–$C_3$); $R_3$ is hydroxy or alkanoyloxy($C_2$–$C_6$); $R_4$ is trifluoromethyl, halogen, hydroxy, alkyl($C_1$–$C_6$), phenyl, benzyl, phenoxy, phenylthio, cycloalkyl ($C_3$–$C_6$), 2,4-dichlorophenoxy or mono- and di-substituted phenyl wherein the substituents are halogen or alkoxy($C_1$–$C_3$); and $R_5$ is hydrogen, or halogen; with the proviso that when $R_1$ is hydrogen, bromo or methyl and $R_2$ is other than fluoro and $R_3$ is hydroxy then $R_4$ may not be chloro, bromo, iodo, methyl or phenyl.

2. The compound according to claim 1; 6-fluoro-3-hydroxy-2-[1,1'-biphenyl]-4-yl-4-quinolinecarboxylic acid.

3. The compound according to claim 1; 3-acetyloxy)-2-[1,1'-biphenyl]-4-yl-4-quinolinecarboxylic acid.

4. The compound according to claim 1; 6,8-dichloro-3-hydroxy-2-[1,1'-biphenyl]-4-yl-4-quinolinecarboxylic acid.

5. The compound according to claim 1; 8-methyl-3-hydroxy-2-[1,1'-biphenyl]-4-yl-4-quinolinecarboxylic acid.

6. The compound according to claim 1; 6-fluoro-3-hydroxy-2-(2'-fluoro-[1,1'-biphenyl]-4-yl)-4-yl)-4-quinolinecarboxylic acid.

7. The compound according to claim 1; 6,8-dichloro-3-hydroxy-2-(3,4-dichlorophenyl)-4-quinoline-carboxylic acid.

8. The compound according to claim 1; 6-bromo-3-(acetyloxy)-2-[1,1'-biphenyl]-4-yl-4-quinoline-carboxylic acid.

9. The compound according to claim 1; 6-fluoro-3-hydroxy-2-(4'-methyoxy-[1,1'-biphenyl]-4yl)-4-quinolinecarboxylic acid.

* * * * *